United States Patent [19]

Yamagishi et al.

[11] Patent Number: 5,767,039
[45] Date of Patent: Jun. 16, 1998

[54] PROCESS FOR MANUFACTURING METHANOL AND PROCESS FOR MANUFACTURING CATALYST FOR METHANOL SYNTHESIS

[75] Inventors: Ken Yamagishi; Yoriko Obata; Yuichi Sugano. all of Niigata, Japan

[73] Assignee: Mitsubishi Gas Chemical Company, Inc., Tokyo, Japan

[21] Appl. No.: 634,604

[22] Filed: Apr. 18, 1996

[30] Foreign Application Priority Data

May 11, 1995 [JP] Japan ................... 7-113128

[51] Int. Cl.⁶ .................... B01J 23/06; B01J 23/72
[52] U.S. Cl. ................ 502/342; 502/343; 502/345; 502/346
[58] Field of Search ................ 502/342, 343, 502/345, 346, 355

[56] References Cited

U.S. PATENT DOCUMENTS

| | | | |
|---|---|---|---|
| 3,066,012 | 11/1962 | Wilson | 23/143 |
| 3,388,972 | 6/1968 | Reitmeier | 23/213 |
| 3,615,217 | 10/1971 | O'Brien | 23/213 |
| 3,923,694 | 12/1975 | Cornthwaite | 252/463 |
| 3,971,735 | 7/1976 | Asano et al. | 252/432 |
| 4,111,847 | 9/1978 | Stiles | 252/463 |
| 4,386,017 | 5/1983 | Nakamura et al. | 252/463 |

FOREIGN PATENT DOCUMENTS

| | | |
|---|---|---|
| 0 381 839 | 8/1990 | European Pat. Off. . |
| 0381839 | 8/1990 | European Pat. Off. ......... C01G 3/00 |
| 0 482 753 | 4/1992 | European Pat. Off. . |
| 30 05 551 | 8/1981 | Germany . |
| 2 025 418 | 1/1980 | United Kingdom . |

OTHER PUBLICATIONS

Database WPI, Section Ch, Week 9512, Derwent Publications Ltd., London, GB; Class E17, AN 95–084551, XP002010269 of JP-A-07 008 799 (Mitsubishi Jukogyo KK), 13 Jan. 1995.

Database WPI, Section Ch, Week 9118, Derwent Pubications Ltd., London, GB; Class E17, AN 91–129072, XP002010270 of JP-A-03 068 450 (Mitsubishi Heavy IND KK), 25 Mar. 1991.

Kiennemann et al., "Methanol Synthesis on $Cu/ZnAl_2O_4$ and $Cu/ZnO—AL_2O_3$ Catalysts", Applied Catalysis, vol. 59, No. 1, 12 Mar. 1990, pp. 165–184, XP 000578631.

J. –L. Li et al. "Characterization of precursors of methanol synthesis catalysts, copper/zinc/aluminum oxides, precipitated at different pHs and temperatures", Applied Catalysis, vol. 137, No. 1, 28 Mar. 1996, pp. 105–117, XP 000578630.

R. H. Höppener et al, "Preparation and Characterization of Stable Copper/Zinc Oxice/Alumina Catalysts for Methanol Synthesis", Applied Catalysis, vol. 25, No. 1–2, 15 Aug. 1986, pp. 109–119, XP 00578632.

*Primary Examiner*—Glenn Caldarola
*Assistant Examiner*—Alexander G. Ghyka
*Attorney, Agent, or Firm*—Fishauf, Holtz, Goodman, Langer & Chick, P.C.

[57] ABSTRACT

A process for manufacturing methanol is herein disclosed which comprises the step of reacting hydrogen with carbon monoxide and/or carbon dioxide in the presence of a synthetic catalyst obtainable by mixing, in a slurry state, (a) a beforehand prepared precipitation slurry of copper and zinc, with (b) an alumina precursor separately prepared from a water-soluble aluminum salt and a basic precipitant, to obtain a composition containing copper, zinc and aluminum, and washing, drying and then calcining the composition. A process for manufacturing the above-mentioned catalyst is also disclosed. According to the present invention, methanol can extremely efficiently be manufactured, and the catalyst having a high activity and an excellent heat resistance can also be manufactured.

17 Claims, No Drawings

PROCESS FOR MANUFACTURING METHANOL AND PROCESS FOR MANUFACTURING CATALYST FOR METHANOL SYNTHESIS

BACKGROUND OF THE INVENTION

1. Field of the Invention

The present invention mainly relates to a process for manufacturing methanol by the reaction of $H_2$ with CO and/or $CO_2$, and a process for manufacturing a copper-zinc-aluminum synthetic catalyst for use in the synthetic reaction of the above-mentioned manufacture or the like.

2. Description of the Related Arts

As catalysts for the synthesis of methanol by the reaction of $H_2$ with CO and/or $CO_2$, copper catalysts have usually been used, and for the purpose of improving the activity and the strength of the catalyst or for the purpose of rationalizing its manufacturing process, various catalyst manufacturing methods have been suggested.

Heretofore, as the catalysts for the methanol synthesis, zinc-chromium catalysts and copper-zinc-chromium catalysts have been used, but in recent years, copper-zinc-aluminum catalysts have often been used. For example, in Japanese Patent Publication No. 16682/1970 (UK Patent No. 1159035) and Japanese Patent Publication No. 23263/1973 (UK Patent No. 1286970), a copper-zinc-aluminum catalyst has been described, and in Japanese Patent Publication No. 44715/1976 (U.S. Pat. No. 3,971,735), a copper-zinc-aluminum-boron catalyst has been described.

Furthermore, in Japanese Patent Publication No. 10256/1984 (U.S. Pat. No. 4,386,017), manufacturing methods of a copper-zinc-aluminum catalyst and a copper-zinc-aluminum-boron catalyst have been described in which an inexpensive and water-insoluble zinc compound such as zinc oxide or zinc hydroxide is used as a zinc source and carbon dioxide is blown into the zinc compound. In Japanese Patent Publication No. 39287/1988, a catalyst having heightened catalytic activity and mechanical strength has been described which can be obtained by adding a specific amount of silicon to copper-zinc components.

Nowadays, in order to promote the enlargement and the cost reduction of the process for the methanol synthesis, the decrease in an energy unit has been intended and a method for industrially advantageously manufacturing a high-performance catalyst has been developed. In general, the manufacturing process of the catalyst for the methanol synthesis can roughly be divided into three steps of (1) a step of producing a cake or a slurry via a precipitation reaction, (2) a step of forming a material powder for molding by drying, calcining and grinding the cake or the slurry, and (3) a molding step for the formation of tablets. Particularly in a conventional method for manufacturing a copper-zinc-aluminum catalyst, it is known that the production conditions and the production manner of the cake or the slurry in the above-mentioned step (1) have a large influence on the catalytic performances of activity, selectivity, strength, life and the like. The reaction for the methanol synthesis is an exothermic reaction, and so the resistance of the catalyst to heat is one of important factors which industrially practical catalysts should possess.

An object of the present invention is to provide an extremely efficient process for manufacturing methanol, and another object of the present invention is to provide a process for manufacturing an industrially useful catalyst for methanol synthesis having a high activity and heat resistance.

SUMMARY OF THE INVENTION

The present inventors have intensively researched a process for manufacturing methanol and a process for manufacturing a catalyst for methanol synthesis with the intention of solving the above-mentioned problems, and as a result, it has been found that a catalyst having an improved methanol synthesis activity and an improved heat resistance can be manufactured by mixing, in a slurry state, a beforehand prepared precipitation slurry of copper and zinc with an alumina precursor separately prepared from a water-soluble aluminum salt and a basic precipitant to obtain a composition, and washing, drying and then calcining the obtained composition. In consequence, the present invention has been attained on the basis of this knowledge.

That is to say, according to the present invention, there can be provided a process for manufacturing methanol which comprises the step of reacting hydrogen with carbon monoxide, carbon dioxide or both of carbon monoxide and carbon dioxide in the presence of a synthetic catalyst obtainable by mixing, in a slurry state, (a) a beforehand prepared precipitation slurry of copper and zinc, with (b) an alumina precursor separately prepared from a water-soluble aluminum salt and a basic precipitant to obtain a composition, and washing, drying and then calcining the composition. In the present invention, hydrogen is preferably reacted with carbon monoxide and/or carbon dioxide in the presence of the synthetic catalyst at a temperature of 150° to 350° C.

Furthermore, according to the present invention, there can be provided a process for manufacturing a catalyst for methanol synthesis and a copper-zinc-aluminum catalyst which comprises the steps of mixing, in a slurry state, (a) a beforehand prepared precipitation slurry of copper and zinc with (b) an alumina precursor separately prepared from a water-soluble aluminum salt and a basic precipitant to obtain a composition containing copper, zinc and aluminum, and washing, drying and then calcining the composition.

Here, the composition obtained by the mixing in the slurry state may contain, in addition to copper, zinc and aluminum, boron and/or silicon for the improvement of a catalytic activity, strength and the like. If necessary, a compound of Mg, Zr, La, Mn, Cr or P can be added to the composition.

In addition, the above-mentioned water-soluble aluminum salt is preferably aluminum nitrate, aluminum sulfate or aluminum chloride, and the above-mentioned basic precipitant is preferably sodium carbonate, ammonium carbonate, sodium hydroxide or aqueous ammonia.

DESCRIPTION OF PREFERRED EMBODIMENTS

In the first place, reference will be made to a composition for use in the present invention which can be obtained by mixing, in a slurry state, (a) a beforehand prepared precipitation slurry of copper and zinc with (b) an alumina precursor separately prepared from a water-soluble aluminum salt and a basic precipitant.

The slurry of copper and zinc in the above-mentioned preparation step of the composition can be prepared from an aqueous solution containing copper and zinc by suitably employing a known method such as a method which comprises a precipitation step by the use of, for example, a potassium carbonate precipitant, or a method which comprises adding a zinc oxide slurry to a copper precipitation slurry, and then carbonating the mixture with carbon dioxide. The alumina precursor can be prepared from an aqueous solution containing aluminum by the use of, for example, an alkali hydroxide or an alkali carbonate. The mixing of the slurry of copper and zinc with the alumina precursor is carried out in a slurry state so that both the materials may uniformly be mixed. Furthermore, a boron compound and a silicon compound can be added to a copper source, a zinc source, an aluminum source or the like, and the silicon compound can suitably be added in a kneading step which will hereinafter be described.

With regard to the composition of the catalyst according to the present invention, an atomic ratio of copper:zinc is in the range of 0.2 to 12:1, preferably 0.3 to 7:1.

With regard to the component contents of copper, zinc and aluminum in terms of atoms, a copper content is 35 to 80%, a zinc content is 15 to 50%, preferably 20 to 40%, and an aluminum content is 1 to 20%, preferably 4 to 16%.

In the case that the precipitation slurry comprises copper, zinc, aluminum and boron, the component contents in terms of atoms are 30 to 80%, preferably 40 to 70% of copper, 15 to 50%, preferably 20 to 40% of zinc, 1 to 20%, preferably 4 to 16% of aluminum, and 0.3 to 5%, preferably 0.5 to 3% of boron.

In the case that the precipitation slurry comprises copper, zinc, aluminum, boron and silicon, the component contents in terms of atoms are 35 to 80%, preferably 40 to 70% of copper, 15 to 50%, preferably 20 to 40% of zinc, 1 to 20%, preferably 4 to 16% of aluminum, 0.3 to 5%, preferably 0.5 to 3% of boron, and 0.1 to 3.5%, preferably 0.5 to 3% of silicon.

Examples of the copper source which can be used in the present invention include water-soluble salts such as copper nitrate, copper sulfate and copper acetate, but copper sulfate which is inexpensive is particularly advantageous. Examples of the usable zinc source include water-soluble salts such as zinc nitrate, zinc sulfate and zinc acetate as well as inexpensive zinc oxide. Furthermore, examples of the usable aluminum source include water-soluble salts such as aluminum nitrate, aluminum sulfate and aluminum acetate. Examples of the usable boron source include boric acid and borax. In addition, examples of the usable silicon source include silicon oxides and precursors of the silicon oxides, but products obtained by the double decomposition of sodium silicate, and diatomaceous earth are particularly advantageous.

Moreover, if necessary, in the catalyst of the present invention, there can be added a precursor of an oxide of Mg, Zr, La, Mn, Cr or the like, for example, a carbonate, or an oxyacid salt of phosphorus.

In the manufacture of the catalyst according to the present invention, examples of the precipitant which can be used together with the aqueous metallic salt solution containing the above-mentioned components include carbonates of alkali metals and ammonium as well as combinations of alkali hydroxides and carbon dioxide. The amount of the precipitant to be used is once to twice, preferably 1.1 to 1.6 times as much as the equivalent of the metallic salt.

A temperature for the formation of the precipitate is in the range of 20° to 90° C., preferably 35° to 80° C. In this case, each concentration of the aqueous metallic salt solution and the precipitant is preferably in the range of 0.2 to 3 mol/liter, preferably 0.5 to 2 mol/liter.

The present invention is directed to a process for manufacturing the catalyst for methanol synthesis which comprises the steps of mixing, in the slurry state, the beforehand prepared precipitation slurry of copper and zinc, with the alumina precursor separately prepared from the water-soluble aluminum salt and the basic precipitant to obtain the composition containing copper, zinc and aluminum, and washing, drying and then calcining the composition. The mixing technique of the precipitation slurry of copper and zinc, with the alumina precursor is important for a catalytic performance, and the mixing of these materials in the slurry state leads to an intimate mixing state, which enables the improvement of the catalytic performance.

As the mixing technique of the precipitation slurry of copper and zinc, with an alumina precursor compound, there are, for example, a manner of precipitating copper and zinc in the presence of the alumina precursor compound, and a manner of preparing an aqueous three-component solution of the copper, zinc and aluminum sources, and then precipitating them simultaneously. In these manners, however, the intimateness between copper and zinc as well as the intimateness among copper, zinc and the alumina precursor compound is impaired owing to the presence of the alumina precursor compound, so that the activity of the obtained catalyst deteriorates.

That is to say, in place of the alumina precursor prepared by the present invention, if another alumina precursor compound, for example, a commercially available alumina sol (Nissan Chemical Industries Ltd.), Cataloid (Catalysts & Chemicals Ind. Co., Ltd.) or aluminum hydroxide is used, the accomplishment of the intimate mixing is difficult, so that the effect of the present invention cannot be sufficiently attained.

A temperature at which the precipitation slurry of copper and zinc is mixed with the alumina precursor can be selected in the range of room temperature to 90° C., and it is preferably in the range of 30° to 85° C.

The mixed slurry obtained by the above-mentioned operation is usually filtered and then washed. In this case, when a sulfate of copper is used as the material, a diluted aqueous alkali solution, for example, sodium carbonate or sodium hydroxide having a concentration of 0.01 to 0.5% is required to be used.

To the thus produced composition, silicon can be added, if necessary. When the composition is in the state of a cake, a usual mixer such as a kneader or a reciprocating stirrer can be used.

The obtained cake or slurry is dried at a temperature of 50° to 150° C., calcined at a temperature of 180° to 500° C., preferably 200° to 450° C. in an air atmosphere, ground in a known manner, and then subjected to a molding step.

The present invention, as described above, is directed to the process for preparing the catalyst for the methanol synthesis which comprises the steps of mixing, in the slurry state, the beforehand prepared precipitation slurry of copper and zinc with the alumina precursor separately prepared from the water-soluble aluminum salt and the basic precipitant to produce the composition containing copper, zinc and aluminum, and washing, drying and then calcining the composition. According to the process of the present invention, the beforehand prepared precipitation slurry of copper and zinc can be mixed, in the slurry state, with the alumina precursor separately prepared from the water-soluble aluminum salt and the basic precipitant, and therefore copper, zinc and aluminum precipitates can extremely intimately be mixed. As a result, the excellent industrial catalyst having the improved activity and heat resistance can be obtained.

The catalyst of the present invention can be used, for example, as a catalyst for a carbon monoxide conversion reaction, a hydrogenation reaction, or the decomposition or the water vapor modification reaction of methanol, in addition to the above-mentioned methanol synthesis reaction.

Next, explanation will be made about a process for manufacturing methanol by the use of the synthetic catalyst obtained by the above-mentioned manufacturing process.

In the methanol preparation process of the present invention, hydrogen is reacted with carbon monoxide and/or carbon dioxide in the presence of the above dried and calcined synthetic catalyst.

In such a methanol preparation process, the synthetic catalyst is usually subjected to an activation treatment by reduction with hydrogen or carbon monoxide, and the thus treated catalyst is then used in the reaction for synthesizing methanol from a mixed gas of hydrogen and carbon monoxide and/or carbon dioxide. This methanol synthesis reaction is carried out at a temperature of 150° to 350° C., preferably 200° to 300° C. under a pressure of 20 to 300 atm, preferably 30 to 150 atm at a gas space velocity of 2,000 to 50,000 h$^{-1}$.

According to the above-mentioned methanol manufacturing process of the present invention, methanol can extremely efficiently be manufactured, because the above specific synthetic catalyst has a higher initial activity as compared with another catalyst having the same composition and maintains the high activity even after the reaction at a high temperature.

Accordingly, the methanol manufacturing process of the present invention is considered to be excellent from an industrial viewpoint, and hence the industrial significance of the present invention is large.

Next, the present invention will be described in more detail with reference to examples and comparative examples. However, catalytic activity and the like depend upon catalytic components and manufacturing methods thereof, and hence the scope of the present invention is not limited to these examples.

EXAMPLE 1

628 g of copper sulfate pentahydrate and 39 g of boric acid were dissolved in 1.6 liters of ion-exchange water, and the mixture was then adjusted to 40° C. to prepare a solution A. 346 g of anhydrous sodium carbonate was dissolved in 2 liters of ion-exchange water, and the mixture was then adjusted to 40° C. to prepare a solution B. 102 g of zinc oxide was dispersed in 0.6 liter of ion-exchange water, and the mixture was then adjusted to 40° C. to prepare a solution C. 216 g of an aqueous aluminum sulfate solution (alumina content=7.5%) was dissolved in 0.66 liter of ion-exchange water, and the mixture was then adjusted to 40° C. to prepare a solution D. Furthermore, 44 g of sodium hydroxide was dissolved in 0.66 liter of ion-exchange water, and the mixture was then adjusted to 40° C. to prepare a solution E.

The solution A was poured into the solution B with stirring, and the solution C was then added thereto. Immediately, carbon dioxide was blown into the solution at a flow rate of 24 liters/hr, and the solution was heated up to 80° C., maintained at this temperature for 30 minutes, and then cooled to 60° C.

To this slurry, there was added an alumina precursor slurry obtained by adding the solution D to the solution E with stirring, followed by stirring for 20 minutes. Afterward, the slurry was filtered, and the resulting cake was successively washed with 50 liters of a 0.04% aqueous sodium hydroxide solution and further washed with 15 liters of ion-exchange water to obtain a composition cake.

To this cake, 3.5 g of diatomaceous earth was added, and they were mixed by a reciprocating stirrer. This slurry was dried at 100° C. for 16 hours.

The thus dried material was calcined at 380° C. under an air stream, and the calcined grains were then uniformized to 16 mesh or less. Afterward, 3% of graphite was added thereto, and the mixture was then molded into tablets having a diameter of 6 mm and a height of 5 mm to prepare a catalyst A.

Comparative Example 1

628 g of copper sulfate pentahydrate and 39 g of boric acid were dissolved in 1.6 liters of ion-exchange water, and the mixture was then adjusted to 40° C. to prepare a solution A. 346 g of anhydrous sodium carbonate was dissolved in 2 liters of ion-exchange water, and the mixture was then adjusted to 40° C. to prepare a solution B. 102 g of zinc oxide was dispersed in 0.6 liter of ion-exchange water, and the mixture was then adjusted to 40° C. to prepare a solution C. 216 g of an aqueous aluminum sulfate solution (alumina content=7.5%) was dissolved in 0.66 liter of ion-exchange water, and the mixture was then adjusted to 40° C. to prepare a solution D. Furthermore, 44 g of sodium hydroxide was dissolved in 0.66 liter of ion-exchange water, and the mixture was then adjusted to 40° C. to prepare a solution E.

The solution A was added into the solution B with stirring, and the solution E, the solution D and the solution C were successively added thereto. Immediately, carbon dioxide was blown into the solution at a flow rate of 24 liters/hr, and the solution was heated up to 80° C., maintained at this temperature for 30 minutes, and then cooled to 60° C. Afterward, the slurry was filtered, and the resulting cake was successively washed with 50 liters of a 0.04% aqueous sodium hydroxide solution and further washed with 15 liters of ion-exchange water to obtain a composition cake. The subsequent procedure was carried out as in Example 1 to prepare a catalyst B.

Comparative Example 2

628 g of copper sulfate pentahydrate and 39 g of boric acid were dissolved in 1.6 liters of ion-exchange water, and the mixture was then adjusted to 40° C. to prepare a solution A. 346 g of anhydrous sodium carbonate was dissolved in 2 liters of ion-exchange water, and the mixture was then adjusted to 40° C. to prepare a solution B. 102 g of zinc oxide was dispersed in 0.6 liter of ion-exchange water, and the mixture was then adjusted to 40° C. to prepare a solution C. 216 g of an aqueous aluminum sulfate solution (alumina content=7.5%) was dissolved in 0.66 liter of ion-exchange water, and the mixture was then adjusted to 40° C. to prepare a solution D. Furthermore, 44 g of sodium hydroxide was dissolved in 0.66 liter of ion-exchange water, and the mixture was then adjusted to 40° C. to prepare a solution E.

The solution D was added into the solution E with stirring, and the mixture was then stirred at 40° C. for 20 minutes to prepare an alumina precursor slurry. To this slurry, the solution B, the solution A and the solution C were then added in this order. Immediately, carbon dioxide was blown into the solution at a flow rate of 24 liters/hr, and the solution was heated up to 80° C., maintained at this temperature for 30 minutes, and then cooled to 60° C.

Afterward, the slurry was filtered, and the resulting cake was successively washed with 50 liters of a 0.04% aqueous sodium hydroxide solution and further washed with 15 liters of ion-exchange water to obtain a composition cake. The subsequent procedure was carried out as in Example 1 to obtain a catalyst C.

EXAMPLE 2

The same procedure as in Example 1 was repeated except that boric acid was not used and an aqueous aluminum sulfate solution was replaced with aluminum nitrate (nonahydrate) as an aluminum source for the preparation of an alumina precursor to obtain a catalyst D.

Comparative Example 3

The same procedure as in Example 2 was repeated except that a slurry which was not yet mixed with an alumina precursor was filtered and then washed and the alumina precursor was replaced with 162 g of an alumina sol (#200, made by Nissan Chemical Industries Ltd., alumina content= 10%) to obtain a catalyst E.

Comparative Example 4

The same procedure as in Example 2 was repeated except that a slurry which was not yet mixed with an alumina precursor was filtered and then washed and the alumina precursor was replaced with 23 g of Cataloid AP (Catalysts & Chemicals Ind. Co., Ltd., alumina content=70%) to obtain a catalyst F.

EXAMPLE 3

214 g of copper sulfate pentahydrate recovered from a copper etching process and 18.8 g of boric acid were dissolved in 1.5 liters of ion-exchange water, and the mixture was then adjusted to 40° C. to prepare a solution A. 105 g of anhydrous sodium carbonate was dissolved in 1.2 liters of ion-exchange water, and the mixture was then adjusted to 40° C. to prepare a solution B.

49 g of zinc oxide was dispersed in 0.5 liter of ion-exchange water, and the mixture was then adjusted to 40° C. to prepare a solution C. 72 g of an aqueous aluminum sulfate solution (alumina content=7.5%) was dissolved in 0.66 liter of ion-exchange water, and the mixture was then adjusted to 40° C. to prepare a solution D. Furthermore, 15 g of sodium hydroxide was dissolved in 0.66 liter of ion-exchange water, and the mixture was then adjusted to 40° C. to prepare a solution E.

The solution A was added into the solution B with stirring, and the solution C was then added thereto. Immediately, carbon dioxide was blown into the solution at a flow rate of 10 liters/hr, and the solution was heated up to 80° C., maintained at this temperature for 30 minutes, and then cooled to 60° C.

To this slurry, there was added an alumina precursor slurry obtained by adding the solution D to the solution E with stirring, followed by stirring for 20 minutes. Afterward, the slurry was filtered, and the resulting cake was successively washed with 50 liters of a 0.02% aqueous sodium hydroxide solution and further washed with 10 liters of ion-exchange water to obtain a composition cake.

The cake was dried and then calcined at 380° C. under an air stream, and the calcined grains were then uniformized to 16 mesh or less. Afterward, 3% of graphite was added thereto, and the mixture was then molded into tablets having a diameter of 6 mm and a height of 5 mm to obtain a catalyst G.

Comparative Example 5

214 g of copper sulfate pentahydrate recovered from a copper etching process and 18.8 g of boric acid were dissolved in 1.5 liters of ion-exchange water, and the mixture was then adjusted to 40° C. to prepare a solution A. 105 g of anhydrous sodium carbonate was dissolved in 1.2 liters of ion-exchange water, and the mixture was then adjusted to 40° C. to prepare a solution B.

49 g of zinc oxide was dispersed in 0.5 liter of ion-exchange water, and the mixture was then adjusted to 40° C. to prepare a solution C. 72 g of an aqueous aluminum sulfate solution (alumina content=7.5%) was dissolved in 0.66 liter of ion-exchange water, and the mixture was then adjusted to 40° C. to prepare a solution D. Furthermore, 15 g of sodium hydroxide was dissolved in 0.66 liter of ion-exchange water, and the mixture was then adjusted to 40° C. to prepare a solution E.

The solution A was poured into the solution B with stirring, and the solution E and the solution D were successively added thereto in this order. After the solution was allowed to stand for 60 minutes, the solution C was added. Immediately, carbon dioxide was blown into the solution at a flow rate of 10 liters/hr, and the solution was heated up to 80° C., maintained at this temperature for 30 minutes, and then cooled to 60° C.

Afterward, the solution was filtered, and the resulting cake was successively washed with 50 liters of a 0.02% aqueous sodium hydroxide solution and further washed with 10 liters of ion-exchange water to obtain a composition cake. The subsequent procedure was carried out as in Example 2 to obtain a catalyst H.

EXAMPLE 4

1.95 kg of copper nitrate trihydrate was dissolved in 14.9 liters of ion-exchange water, and the mixture was then adjusted to 0° C. to prepare a solution A. 1.3 kg of ammonium bicarbonate was dissolved in 11.3 liters of ion-exchange water, and the mixture was then adjusted to 40° C. to prepare a solution B. 0.5 kg of zinc oxide was dispersed in 4 liters of ion-exchange water, and the mixture was then adjusted to 40° C. to prepare a solution C. 375 g of aluminum nitrate nona-hydrate was dissolved in 6 liters of ion-exchange water, and the mixture was then adjusted to 40° C. to prepare a solution D. Furthermore, 96 g of sodium hydroxide was dissolved in 6 liters of ion-exchange water, and the mixture was then adjusted to 40° C. to prepare a solution E.

The solution A was poured into the solution B with stirring, and the solution C was then added thereto. Immediately, carbon dioxide was blown into the solution for 2 hours at a flow rate of 30 liters/hr. Next, the solution was heated up to 80° C., maintained at this temperature for 30 minutes, and then cooled to 60° C. To this slurry, there was added an alumina precursor slurry obtained by adding the solution D to the solution E with stirring, followed by stirring for 30 minutes. Afterward, the slurry was filtered, and the resulting cake was successively washed with a aqueous solution, and the slurry was then dried at 100° C. for 18 hours.

The dried material was calcined at 380° C. under an air stream, and the calcined grains were then uniformized to 16 mesh or less. Afterward, 3% of graphite was added thereto, and the mixture was then molded into tablets having a diameter of 6 mm and a height of 5 mm to obtain a catalyst I.

Comparative Example 6

1.95 kg of copper nitrate trihydrate was dissolved in 14.9 liters of ion-exchange water, and the mixture was then adjusted to 0° C. to prepare a solution A. 1.3 kg of ammonium bicarbonate was dissolved in 11.3 liters of ion-exchange water, and the mixture was then adjusted to 40° C. to prepare a solution B. 0.5 kg of zinc oxide was dispersed in 4 liters of ion-exchange water, and the mixture was then adjusted to 40° C. to prepare a solution C. 375 g of aluminum nitrate nona-hydrate was dissolved in 6 liters of ion-exchange water, and the mixture was then adjusted to 40° C. to prepare a solution D. Furthermore, 96 g of sodium hydroxide was dissolved in 6 liters of ion-exchange water, and the mixture was then adjusted to 40° C. to prepare a solution E.

The solution D was poured into the solution E with stirring, and the mixture was then stirred at 40° C. for 20 minutes to prepare an alumina precursor slurry. To this slurry, the solution C was added, and immediately, carbon dioxide was blown into the solution at a flow rate of 24 liters/hr, and the solution was then maintained with stirring for 30 minutes. Next, the solution B and the solution A were poured thereinto in this order and then maintained for 30 minutes. Afterward, the solution was heated up to 80° C., maintained at this temperature for 30 minutes, and then cooled to 60° C. The subsequent procedure was carried out as in Example 4 to obtain a catalyst J.

EXAMPLE 5

3.6 kg of copper nitrate trihydrate, 3.3 kg of zinc nitrate (hexahydrate) and 0.7 kg of boric acid were dissolved in 37 liters of ion-exchange water to prepare a solution A. 3.3 kg of anhydrous sodium carbonate was dissolved in 126 liters of ion-exchange water to prepare a solution B. 0.55 kg of aluminum nitrate nona-hydrate was dissolved in 3 liters of ion-exchange water, and the mixture was then adjusted to 40° C. to prepare a solution C. 0.28 g of anhydrous sodium carbonate was dissolved in 3 liters of ion-exchange water, and the mixture was then adjusted to 40° C. to prepare a solution D.

The solution A was poured into the solution B with stirring, and the solution was heated up to 80° C., maintained at this temperature for 30 minutes, and then cooled to 50° C. To this slurry, there was added an alumina precursor slurry obtained by adding the solution C to the solution D with stirring, followed by stirring for 30 minutes. Afterward, the slurry was filtered, and the resulting cake was successively washed with a aqueous solution, and the slurry was then dried at 110° C. for 16 hours.

The dried material was calcined at 380° C. under an air stream, and the calcined grains were then uniformized to 16 mesh or less. Afterward, 3% of graphite was added thereto, and the mixture was then molded into tablets having a diameter of 6 mm and a height of 5 mm to obtain a catalyst K.

Comparative Example 7

3.6 kg of copper nitrate trihydrate, 3.3 kg of zinc nitrate hexahydrate, 0.7 kg of boric acid and 0.55 kg of aluminum nitrate nona-hydrate were dissolved in 40 liters of ion-exchange water to prepare a solution A. 3.58 kg of anhydrous sodium carbonate was dissolved in 129 liters of ion-exchange water to prepare a solution B.

The solution A was poured into the solution B with stirring, and the solution was heated up to 80° C., maintained for 30 minutes, and then cooled to 50° C. Afterward, the slurry was filtered and then washed, and the subsequent procedure was carried out as in Example 5 to obtain a catalyst L.

EXAMPLES 6 TO 10

Comparative Examples 8 to 14

Each catalyst prepared by the above-mentioned process was ground to 20-40 mesh, maintained at 140° C. in a nitrogen gas stream, and then finally maintained at 240° C. for 3 hours in hydrogen whose concentration had been lowered to inhibit a rapid exothermic phenomenon, thereby reducing the catalyst.

Next, in order to inspect an initial activity, the synthetic reaction of methanol was carried out. As a material gas, there was used a mixed gas comprising 70% of hydrogen, 22% of carbon monoxide and 5% of carbon dioxide, and a reaction pressure, a gas space velocity and a reaction temperature were set to 70 atm, 20,000 hr$^{-1}$ and 260° C., respectively.

Furthermore, in order to inspect the heat resistance of the catalyst, methanol was synthesized at a catalyst temperature of 360° C. for 2 hours, and afterward, the catalyst temperature was raised to 260° C. again and at this time, the catalytic activity was measured. Moreover, after the reaction was carried out at 360° C. for 4 hours (6 hours in total), the catalytic activity at 260° C. was measured. In addition, after the reaction was carried out at 360° C. for 4 hours (10 hours in total), the catalytic activity at 260° C. was measured.

The measured results of the catalytic activity and the heat resistance test are shown in Table 1.

TABLE 1

| Methanol Concentration (mol %) in Reactor Outlet Gas | | | | | |
|---|---|---|---|---|---|
| | | Initial | Reaction at 360° C. for | | |
| | Catalyst | stage | 2 hours | 6 hours | 10 hours |
| Example 6 | A | 20.5 | 19.6 | 19.0 | 18.4 |
| Comp. Ex. 8 | B | 17.5 | 16.6 | 15.8 | 15.0 |
| Comp. Ex. 9 | C | 17.4 | 16.7 | 15.7 | 15.0 |
| Example 7 | D | 20.4 | 19.7 | 19.0 | 18.7 |
| Comp. Ex. 10 | E | 19.4 | 18.6 | 17.8 | 17.1 |
| Comp. Ex. 11 | F | 18.5 | 17.6 | 17.0 | 16.4 |
| Example 8 | G | 15.8 | 15.0 | 14.8 | 14.5 |
| Comp. Ex. 12 | H | 13.6 | 12.8 | 12.2 | 11.8 |
| Example 9 | I | 16.0 | 15.3 | 14.7 | 14.2 |
| Comp. Ex. 13 | J | 14.1 | 13.2 | 12.6 | 12.1 |
| Example 10 | K | 15.5 | 14.6 | 14.2 | 13.8 |
| Comp. Ex. 14 | L | 13.8 | 13.0 | 12.7 | 12.4 |

What is claimed is:

1. A process for manufacturing a catalyst for methanol synthesis which comprises the steps of mixing, in a slurry state, (a) a beforehand prepared precipitation slurry of copper and zinc, with (b) an alumina precursor separately prepared from a water-soluble aluminum salt and a basic precipitant, to obtain a composition containing copper, zinc and aluminum, and washing, drying and then calcining the composition to prepare said catalyst.

2. The process for manufacturing a catalyst for methanol synthesis according to claim 1 wherein the composition obtained by the mixing in the slurry state contains not only copper, zinc and aluminum but also boron, silicon or both of boron and silicon.

3. The process for manufacturing a catalyst for methanol synthesis according to claim 2 wherein the composition obtained by the mixing in the slurry state contains at least one compound selected from the group consisting of compounds of Mg, Zr, La, Mn, Cr and P.

4. The process for manufacturing a catalyst for methanol synthesis according to claim 1 wherein the water-soluble aluminum salt is at least one compound selected from the group consisting of aluminum nitrate, aluminum sulfate and aluminum chloride.

5. The process for manufacturing a catalyst for methanol synthesis according to claim 1 wherein the basic precipitant is at least one compound selected from the group consisting of sodium carbonate, ammonium carbonate, sodium hydroxide and aqueous ammonia.

6. A catalyst which is prepared in accordance with the process of claim 1.

7. The process for manufacturing a catalyst for methanol synthesis according to claim 1 wherein the copper and zinc are in an atomic ratio of 0.2 to 12:1 of copper:zinc.

8. The process for manufacturing a catalyst for methanol synthesis according to claim 7 wherein the ratio is 0.3 to 7:1.

9. The process for manufacturing a catalyst for methanol synthesis according to claim 1 wherein the basic precipitant is selected from the group consisting of an alkali hydroxide and an alkali carbonate.

10. The process for manufacturing a catalyst for methanol synthesis according to claim 1 wherein the mixing of the precipitation slurry and the alumina precursor is carried out at a temperature of 30° to 85° C.

11. The process for manufacturing a catalyst for methanol synthesis according to claim 4 wherein the precipitation slurry of copper and zinc is prepared from a copper source selected from the group consisting of copper nitrate, copper sulfate, and copper acetate; and a zinc source selected from the group consisting of zinc nitrate, zinc sulfate, zinc acetate and zinc oxide.

12. The process for manufacturing a catalyst for methanol synthesis according to claim 11 wherein the copper, zinc and aluminum, in terms of atoms, are contained in the following amounts: a copper content of 35 to 80%, a zinc content of 15 to 50% and an aluminum content of 1 to 20%.

13. The process for manufacturing a catalyst for methanol synthesis according to claim 11 wherein during the process, at least one compound selected from the group consisting of a boron compound and a silicon compound, is introduced.

14. The process for manufacturing a catalyst for methanol synthesis according to claim 4 wherein the basic precipitant is at least one compound selected from the group consisting of sodium carbonate, ammonium carbonate, sodium hydroxide and aqueous ammonia.

15. The process for manufacturing a catalyst for methanol synthesis according to claim 1 wherein the drying is carried out at a temperature of 50° to 150° C. and the calcining is carried out at a temperature of 180° to 500° C.

16. The process for manufacturing a catalyst for methanol synthesis according to claim 2 wherein the precipitation slurry comprises copper, zinc, aluminum and boron in the following amounts in terms of atoms: 40 to 70% of copper, 20 to 40% of zinc, 4 to 16% of aluminum and 0.5 to 3% of boron.

17. The process for manufacturing a catalyst for methanol synthesis according to claim 2 wherein the precipitation slurry comprises copper, zinc, aluminum, boron and silicon in the following amounts in terms of atoms: 40 to 70% of copper, 20 to 40% of zinc, 4 to 16% of aluminum, 0.5 to 3% of boron and 0.5 to 3% of silicon.

\* \* \* \* \*